United States Patent
Martinez et al.

(10) Patent No.: US 6,764,673 B2
(45) Date of Patent: Jul. 20, 2004

(54) SYNTHESIS OF [$^2H_1$, $^{13}C$], [$^2H_2$, $^{13}C$] AND [$^2H_3$, $^{13}C$]METHYL ARYL SULFONES AND SULFOXIDES

(75) Inventors: Rodolfo A. Martinez, Santa Fe, NM (US); Marc A. Alvarez, Santa Fe, NM (US); Louis A. Silks, III, Los Alamos, NM (US); Clifford J. Unkefer, Los Alamos, NM (US); Jurgen G. Schmidt, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/342,521

(22) Filed: Jan. 14, 2003

(65) Prior Publication Data

US 2003/0158445 A1 Aug. 21, 2003

Related U.S. Application Data

(63) Continuation-in-part of application No. 10/074,670, filed on Feb. 13, 2002, now abandoned.

(51) Int. Cl.$^7$ ......................... A61K 51/00; C07C 317/00
(52) U.S. Cl. ......................... 424/1.81; 568/27; 568/28
(58) Field of Search ............................... 424/1.65, 1.81; 568/27, 28

(56) References Cited

U.S. PATENT DOCUMENTS 6,541,671 B1 * 4/2003 Martinez et al. ............... 568/57

OTHER PUBLICATIONS

Journal of the American Chemical Society by Gonzalez-Nunez et al vol. 124 pp. 9154–9163 on Web Jul. 12, 2002.*
CA:129:28153 abs of J. of the Amer. Chem. Soc. by van der Donk et al 120(17) pp 4252–4253 1998.*
CA:118:123892 abs of Inorganic Chem. by Acquaye et al 32(2) pp 160–5 1993.*
CA:111:133927 abs of Journal of Organic Chem. By Satoh et al 54(16) pp 3973–8 1989.*
CA:133:163989 abs of Journal of Labelled Compounds & Radiopharmaceuticals by Chaudhary et al 43(7) pp6833 2000.*
CA:95:97252 abs of Tetrahedron Letters by Trost et al 22(14) pp 1287–90 1981.*

* cited by examiner

Primary Examiner—Jean F. Vollano
(74) Attorney, Agent, or Firm—Bruce H. Cottrell

(57) ABSTRACT

The present invention is directed to labeled compounds, [$^2H_1$, $^{13}C$], [$^2H_2$, $^{13}C$] and [$^2H_3$, $^{13}C$]methyl aryl sulfones and [$^2H_1$, $^{13}C$], [$^2H_2$, $^{13}C$] and [$^2H_3$, $^{13}C$]methyl aryl sulfoxides, wherein the $^{13}C$ methyl group attached to the sulfur of the sulfone or sulfoxide includes exactly one, two or three deuterium atoms and the aryl group is selected from the group consisting of 1-naphthyl, substituted 1-naphthyl, 2-naphthyl, substituted 2-naphthyl, and phenyl groups with the structure:

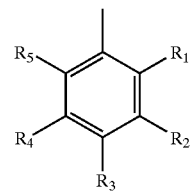

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group. The present invention is also directed to processes of preparing methyl aryl sulfones and methyl aryl sulfoxides.

23 Claims, No Drawings

SYNTHESIS OF [$^2$H$_1$, $^{13}$C], [$^2$H$_2$, $^{13}$C] AND [$^2$H$_3$, $^{13}$C]METHYL ARYL SULFONES AND SULFOXIDES

RELATED APPLICATIONS

This application is a continuation-in-part of application Ser. No. 10/074,670, filed on Feb. 13, 2002, now abandoned by Martinez et al.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to compounds labeled with carbon-13 and hydrogen-2.

BACKGROUND OF THE INVENTION

Stable isotope labeled amino acids and nucleotides are required for structural and mechanistic studies of proteins and oligonucleotides. In addition, isotopically labeled biologically active compounds are required for many phases of drug discovery and development including elucidation of biosynthetic pathways, pharmacokinetics, and drug metabolism. For many applications, site-specific $^{13}$C or combined $^{13}$C and $^2$H labeling are required. While a number of stable isotope labeled compounds are available from companies such as Sigma-Aldrich Chemicals, a need remains for other labeled synthetic precursors.

Methyl aryl sulfones such as methyl phenyl sulfone and methyl aryl sulfoxides such as methyl phenyl sulfoxide have been used in a wide number of reactions to make a large number of such biomolecules and other important synthetic precursors. For example, methyl phenyl sulfone can be used as a nucleophilic synthon and is easily converted into an electrophilic synthon. While methyl phenyl sulfone and methyl phenyl sulfoxide could provide a chemically stable and non-volatile carrier for the valuable $^{13}$C and $^2$H labels, the preparation of few isotopically labeled methyl phenyl sulfones and methyl phenyl sulfoxides has been previously accomplished. One example of isotopically labeled methyl phenyl sulfoxide and methyl phenyl sulfone are shown by Chaudhary et al., J. Labelled Cpd. Radiopharm., 43, 683–691 (2000), although they were not described or suggested as synthetic reagents for synthesis of labeled compounds. Availability of other significant [$^2$H$_1$, $^{13}$C], [$^2$H$_2$, $^{13}$C] and [$^2$H$_3$, $^{13}$C]methyl phenyl sulfones and [$^2$H$_1$, $^{13}$C], [$^2$H$_2$, $^{13}$C] and [$^2$H$_3$, $^{13}$C]methyl phenyl sulfoxides would allow researchers to take advantage of the wealth of chemistry that has been done using unlabeled methyl phenyl sulfone and methyl phenyl sulfoxide.

As carbon-13 is separated from its lighter isotope by cryogenic distillation of carbon monoxide (CO), all labeled carbons are derived ultimately from CO. The highly efficient conversion of CO to useful chemical precursors is perhaps the most unique aspect of stable isotope labeling technology. Any inefficiencies in the early synthetic steps add greatly to the overall expense of isotope labeling. Thus, considerable efforts have been directed to the development of methods for the preparation of useful synthetic precursors or synthons. This effort has given rise to efficient large-scale methods for the synthesis of methane, methanol, methyl iodide, sodium formate, potassium cyanide and carbon dioxide. These methods are the foundation of all labeling chemistry. The most useful of the electrophilic one-carbon precursors, methyl iodide and carbon dioxide, are difficult to store and use efficiently due to their high volatility.

As spectroscopic instrumentation and techniques continue to improve, there is a drive to study ever more complicated bio-systems. This has lead to demands for more complex labeling patterns in biomolecules. In the past, the simple introduction of a labeled atom site-specifically without stereospecificity was the major thrust for stable isotope labeling and the first generation of labeled synthons served this effort well. Increasingly, in today's labeling climate, in addition to site-specific labeling, the requirement for stereospecificity has been added. This includes both the ability to stereospecific label chiral compounds as well as the ability to differentiate between prochiral centers with deuterium or carbon. The development of additional synthons as starting materials will address those growing demands.

Accordingly, it is an object of the present invention to provide labeled compounds.

SUMMARY OF THE INVENTION

In accordance with the purposes of the present invention, as embodied and broadly described herein, the present invention provides labeled compounds, [$^2$H$_1$, $^{13}$C], [$^2$H$_2$, $^{13}$C] and [$^2$H$_3$, $^{13}$C]methyl aryl sulfones wherein the $^{13}$C methyl group attached to the sulfur of the sulfone includes exactly one, two or three deuterium atoms and the aryl group is selected from the group consisting of 1-naphthyl, substituted 1-naphthyl, 2-naphthyl, substituted 2-naphthyl, and phenyl groups with the structure

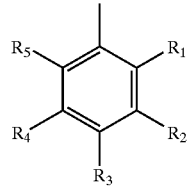

wherein R$_1$, R$_2$, R$_3$, R$_4$ and R$_5$ are each independently, hydrogen, a C$_1$–C$_4$ lower alkyl, a halogen, an amino group from the group consisting of NH$_2$, NHR and NRR' where R and R' are each a C$_1$–C$_4$ lower alkyl, a phenyl, or an alkoxy group.

The present invention further provides a process of preparing methyl aryl sulfone by reacting a methyl aryl sulfide with an oxidizing agent of potassium peroxymonosulfate to form a methyl aryl sulfone.

The present invention still further provides labeled compounds, [$^2$H$_1$, $^{13}$C], [$^2$H$_2$, $^{13}$C] and [$^2$H$_3$, $^{13}$C]methyl aryl sulfoxides wherein the $^{13}$C methyl group attached to the sulfur of the sulfoxide includes exactly one, two or three deuterium atoms and the aryl group is selected from the group consisting of 1-naphthyl, substituted 1-naphthyl, 2-naphthyl, substituted 2-naphthyl, and phenyl groups with the structure:

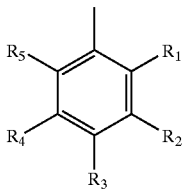

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group.

The present invention further provides a process of preparing methyl aryl sulfoxide by reacting a methyl aryl sulfide with hydrogen peroxide to form a methyl aryl sulfoxide.

DETAILED DESCRIPTION

Methyl aryl sulfones and methyl aryl sulfoxides are useful organic reagents that allow for the preparation of many biochemicals and materials. Isotopically labeled methyl aryl sulfones and methyl aryl sulfoxides can be used to introduce a carbon-13 [$^{13}C$] and a hydrogen-2 or deuterium label [$^2H$] into such biochemicals and materials. As used herein, the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically, the term "aryl" includes, but is not limited to 1-naphthyl, substituted 1-naphthyl, 2-naphthyl, substituted 2-naphthyl, and phenyl groups with the structure

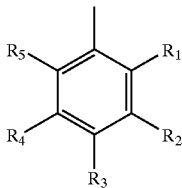

wherein $R_1$, $R_2$, $R_3$, $R_4$ and $R_5$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above.

As used herein, the term "[$^2H_1$, $^{13}C$]" means exactly one deuterium atom, the term "[$^2H_2$, $^{13}C$]" means exactly two deuterium atoms, and the term "[$^2H_3$, $^{13}C$]" means exactly three deuterium atoms within the respective compound.

[$^2H_1$, $^{13}C$], [$^2H_2$, $^{13}C$] and [$^2H_3$, $^{13}C$]methyl aryl sulfones can be made from [$^2H_1$, $^{13}C$], [$^2H_2$, $^{13}C$] and [$^2H_3$, $^{13}C$] methyl aryl sulfides in a one step process as shown below. Such a process can involve reaction of the sulfide with a mild oxidizing agent such as Oxone® (potassium peroxymonosulfate) at room temperature for from several hours up to several days. Other reaction temperatures may be used if desired. Such [$^2H_1$, $^{13}C$], [$^2H_2$, $^{13}C$] and [$^2H_3$, $^{13}C$]methyl aryl sulfones can be used as a non-volatile carrier of the desired carbon and hydrogen labels. Methyl aryl sulfones without the isotopic substitution can be made in high yields by the same process.

$^{13}CD_3$S-aryl→$^{13}CD_3SO_2$-aryl Oxone®

[$^2H_1$, $^{13}C$], [$^2H_2$, $^{13}C$] and [$^2H_3$, $^{13}C$]methyl aryl sulfoxides can also be made from [$^2H_1$, $^{13}C$], [$^2H_2$, $^{13}C$] and [$^2H_3$, $^{13}C$]methyl aryl sulfides in a one step process as shown below. Such a process can involve reaction of the sulfide with hydrogen peroxide at room temperature for several hours. Other reaction temperatures may be used if desired. Such [$^2H_1$, $^{13}C$], [$^2H_2$, $^{13}C$] and [$^2H_3$, $^{13}C$]methyl aryl sulfoxides can be used as a non-volatile carrier of the desired carbon and hydrogen labels. Methyl aryl sulfoxides without the isotopic substitution can be made in high yields by the same process.

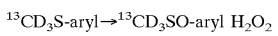

$^{13}CD_3$S-aryl→$^{13}CD_3$SO-aryl $H_2O_2$

Availability of the [$^2H_1$, $^{13}C$], [$^2H_2$, $^{13}C$] and [$^2H_3$, $^{13}C$]methyl aryl sulfones having the structure:

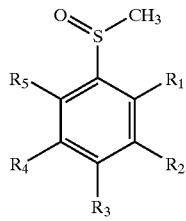

wherein $R_1$, $R_2$, $R_3$, $R_4$ and $R_5$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above, and the methyl group attached to the sulfide includes exactly one, two or three deuterium atoms and [$^2H_1$, $^{13}C$], [$^2H_2$, $^{13}C$] and [$^2H_3$, $^{13}C$]methyl aryl sulfoxides having the structure

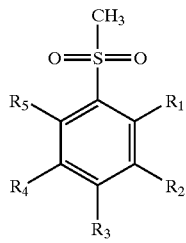

wherein $R_1$, $R_2$, $R_3$, $R_4$ and $R_5$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above, and the $^{13}C$ methyl group attached to the sulfur of the sulfide includes exactly one, two or three deuterium atoms will allow researchers to take advantage of the wealth of chemistry that has been done using unlabeled methyl aryl sulfones and unlabeled methyl aryl sulfoxides.

The present invention provides [$^2H_1$, $^{13}C$], [$^2H_2$, $^{13}C$] and [$^2H_3$, $^{13}C$]methyl aryl sulfones, i.e., [$^{13}C$]methyl aryl sulfone wherein the $^{13}C$ methyl group attached to the sulfur group of the sulfone includes exactly one, two or three deuterium atoms. For those molecules with exactly one or two deuterium atoms, such isotopically differentiated methyl groups can be attractive for a variety of applications. For example, a chirally differentiated isopropyl group, i.e., —CH($^{13}CDH_2$)($^{13}CD_2H$) can be produced.

Similarly, the present invention provides [$^2H_1$, $^{13}C$], [$^2H_2$, $^{13}C$] and [$^2H_3$, $^{13}C$]methyl aryl sulfoxides, i.e., [$^{13}C$]methyl aryl sulfoxide wherein the $^{13}C$ methyl group attached to the sulfur of the sulfoxide includes exactly one, two or three deuterium atoms. As noted before, for those molecules with exactly one or two deuterium atoms, such isotopically differentiated methyl groups can be attractive for a variety of applications.

The present invention provides efficient large scale one-pot processes for the preparation of methyl aryl sulfones, e.g., [$^2H_1$, $^{13}C$], [$^2H_2$, $^{13}C$] and [$^2H_3$, $^{13}C$]methyl aryl sulfones from [$^2H_1$, $^{13}C$], [$^2H_2$, $^{13}C$] and [$^2H_3$, $^{13}C$]methyl aryl sulfides. Such processes can avoid the inevitable losses resulting from the isolation of labeled methyl iodide. Such methyl aryl sulfones can provide a chemically stable and non-volatile carrier for valuable $^{13}C$ and $^2H$ labels.

In addition, an efficient process for the preparation of methyl aryl sulfones, e.g., [$^2H_1$, $^{13}C$], [$^2H_2$, $^{13}C$] and [$^2H_3$, $^{13}C$]methyl aryl sulfones, by oxidation of [$^2H_1$, $^{13}C$], [$^2H_2$, $^{13}C$] and [$^2H_3$, $^{13}C$]methyl aryl sulfides is provided. In the process of the present invention, [$^2H_1$, $^{13}C$], [$^2H_2$, $^{13}C$] and [$^2H_3$, $^{13}C$]methyl aryl sulfones can be prepared in a high yield (>98%) process by oxidizing [$^2H_1$, $^{13}C$], [$^2H_2$, $^{13}C$] and [$^2H_3$, $^{13}C$]methyl aryl sulfides to produce [$^2H_1$, $^{13}C$], [$^2H_2$, $^{13}C$] and [$^2H_3$, $^{13}C$]methyl aryl sulfones.

The present invention is more particularly described in the following examples which are intended as illustrative only, since numerous modifications and variations will be apparent to those skilled in the art.

EXAMPLE 1

[$^{13}C$]Methyl phenyl sulfide was prepared as follows. A one-liter, two-neck flask was fitted with an argon inlet adapter and an air-cooled condenser. This flask was charged with 46.2 gram (g) (1.40 mole) of [$^{13}C$]methanol (99% $^{13}C$) and 726 milliliter (ml) (4.20 mole, 3.00 equivalents (eq)) hydriodic acid (HI) (47% by weight solution in water). The air-cooled condenser was fitted with an outlet adapter, which in turn was attached (via a short piece of Tygon® tubing) to a long solvent trap immersed in an ice-water bath. This ice-cooled solvent trap was connected to an inlet adapter on a two-liter, two-neck flask containing a vigorously stirring biphasic mixture of 169.7 g (1.54 mole, 1.10 eq) thiophenol and 140 g (3.50 mol, 2.50 eq) of sodium hydroxide (NaOH) in a mixture of 400 ml benzene and 300 ml water. The second neck of this flask was fitted with an isopropanol/dry ice-cooled condenser with an argon outlet. The [$^{13}C$] methanol/HI solution was then heated at 85° C. for 2 hours, and then heating was discontinued. Again, any [$^{13}C$]methyl iodide, which had collected in the ice-cooled trap was transferred to the sodium-thiophenoxide mixture, and this mixture was allowed to stir overnight. The mixture was then transferred to a separatory funnel containing 400 ml of ethyl ether (Et$_2$O), the organic phase was washed with three 100 ml portions of water, and then dried over sodium sulfate (Na$_2$SO$_4$). Removal of the solvents under reduced pressure gave 168 g (95.6% theoretical yield) of [$^{13}C$]methyl phenyl sulfide as a clear, colorless oil: $^1H$ NMR (500 MHz, CDCl$_3$) $\partial$ 2.33–2.61 (d,3H,J=139.6 Hz), 7.11–7.26(m, 5H); $^{13}C$ NMR (125 MHz, CDCl$_3$) $\partial$ 138.4, 128.8, 126.7, 125.0, 15.9.

EXAMPLE 2

[$^2H_3$, $^{13}C$]Methyl phenyl sulfide was prepared as follows from [$^2H_4$, $^{13}C$]methanol using the procedure of Example 1. From 36.6 g (0.987 mole) of [$^2H_4$, $^{13}C$]methyl alcohol, 540 ml (2.96 mole, 3.00 eq) HI (47% aqueous solution), 120 g (1.09 mole, 1.10 eq) thiophenol, and 98.7 g (2.47 mole, 2.50 eq) NaOH was obtained 125 g (98.6% theoretical yield) [$^2H_3$, $^{13}C$]-methyl phenyl sulfide as a clear, slightly yellow oil: $^1H$ NMR (300 MHz, CDCl$_3$) $\partial$ 7.10–7.26 (m, 5H); $^{13}C$(75 MHz, CDCl$_3$) $\partial$ 138.4, 128.8, 126.7, 125.0, {16.0 15.7, 15.4, 15.1, 14.9, 14.6, 14.3 (septet, J=21.3 Hz)}.

EXAMPLE 3

[$^2H_1$, $^{13}C$]Methyl phenyl sulfide was prepared as follows. A 250 ml round bottom flask fitted with a magnetic stir bar was charged with 5.00 g (39.9 millimoles (mmole)) of [$^{13}C$]methyl phenyl sulfide. About 70 ml of tetrahydrofuran (THF) were added, and the stirred solution was cooled to −78° C. in a dry ice bath. 1.3 M sec-butyl lithium (sec-BuLi) (32.3 ml, 41.9 mmole, 1.05 eq) was added via syringe, and the solution was stirred at −78° C. for 1.5 hours. After this time, the reaction was quenched with 10 ml of $^2H_2O$. The mixture was poured into a separatory funnel containing enough water to dissolve the insoluble material, and the aqueous phase was extracted with two 50 ml portions of methylene chloride (CH$_2$Cl$_2$). The combined organic layers were dried over Na$_2$SO$_4$, and the product (4.98 g, 99% theoretical yield) was obtained through careful removal of the solvents under reduced pressure: $^1H$ NMR (500 MHz, CDCl$_3$) $^{13}C$ NMR (125 MHz, CDCl$_3$) $\partial$ 2.33–2.61 (d, 2H, J=139 Hz), 7.13–7.35 (m, 5H); $^{13}C$ NMR (125 MHz, CDCl$_3$) $\partial$138.3, 128.8, 126.6, 125.0, [15.77, 15.61, 15.43(t, J=21.5 Hz)}.

EXAMPLE 4

[$^2H_2$, $^{13}C$]Methyl phenyl sulfide was prepared as follows. Using the procedure of Example 3, [$^2H_2$, $^{13}C$]methyl phenyl sulfide was prepared from [$^2H_3$, $^{13}C$]methyl phenyl sulfide. From 10.0 g of [$^2H_3$, $^{13}C$]methyl phenyl sulfide (78.0 mmole) and 72 ml of 1.3 M n-BuLi (93.6 mmole, 12 eq) stirring at −78° C. for 3 hours was obtained, after a H$_2$O quench, 9.83 g (99%) of product as a clear, pale-yellow oil; $^1H$ NMR (500 MHz, CDCl$_3$) $\partial$2.30–2.58(d, 1H, J=139 Hz), 7.12–7.29(m, 5H); $^{13}C$ NMR (125 MHz, CDCl$_3$) $^{13}C$ NMR (125 MHz, CDCl$_3$) $\partial$ 138.4, 128.8, 126.6, 125.0, [15.70, 15.53, 15.35, 15.18, 15.01 (pentet, J=21.3 Hz)}.

EXAMPLE 5

[$^{13}C$]Methyl phenyl sulfone was prepared as follows. Oxone® (614.8 g; 0.84 mole/2.5 eq/2.6 eq oxidant) was dissolved in deionized water (750 ml), and ice (250 g) was added. [$^{13}C$]methyl phenyl sulfide (45.0 g, 0.32 mole), dissolved in ethanol (200 ml), was added drop-wise over a period of 3.5 hours via a dropping funnel. The reaction was stirred at room temperature and monitored by thin layer chromatography (TLC) (ether, R$_f$ 0.4) shows complete conversion to the product after 4 hours was poured into a separatory funnel, and the aqueous phase was extracted 2 times with 600 ml portions of ethylacetate. The combined organic phases were dried with Na$_2$SO$_4$ then filtered and solvents evaporated. Remaining solvent was removed from the solid under vacuum using a liquid nitrogen cooled trap.

[$^{13}$C]Methyl phenyl sulfone (53.3 g; 96.4% theoretical yield) was obtained as a white solid, pure by NMR (98%), which could be used in subsequent reactions without further purification $^1$H 300 MHz] 2.832 and 3.293 (3 H $J_{13C-H}$=138 Hz), 7.56–7.69 (3 H, $m_{ABX}$), 7.95 (2H, $J_{ABX}$=7.5 Hz), $^{13}$13C [CDCl$_3$, 75 MHz] 44.66, 127.52, 129.55, 133.89, 140.81 (d, J=8.7 Hz) mp: 84–86° C. [reported literature value for unlabeled material 85–88°]

EXAMPLE 6

[$^2$H$_2$, $^{13}$C]Methyl phenyl sulfone was prepared as follows. Oxone® (240.7 g; 0.40 mole/2.5 eq/2.6 eq oxidant) was dissolved in deionized water (750 ml), and ice (250 g) was added. [$^2$H$_2$, $^{13}$C]methyl phenyl sulfide (20.0 g, 0.156 mole), dissolved in ethanol (200 ml), was added drop-wise over a period of 3.5 hours via a dropping funnel. The reaction was stirred at room temperature and monitored by thin layer chromatography (TLC) (ether, $R_f$ 0.4) shows complete conversion to the product after 4 hours. Then, the reaction mixture was poured into a separatory funnel, and the aqueous phase was extracted 2 times with 600 ml portions of ethylacetate. The combined organic phases were dried with Na$_2$SO$_4$ then filtered and solvents evaporated. Remaining solvent was removed from the solid under vacuum using a liquid nitrogen cooled trap. [$^2$H$_2$, $^{13}$C]Methyl phenyl sulfone (24.44 g; 98% yield) was obtained as a white solid, pure by NMR, which could be used in subsequent reactions without further purification $^1$H 300 MHz] 7.56–7.69 (3 H, $m_{ABX}$), 7.95 (2H, $J_{ABX}$=7.5 Hz), $^{13}$13C [CDCl$_3$, 75 MHz] 44.66 (heptet, J=21 Hz), 127.52, 129.55, 133.89, 140.81 (d, J=8.7 Hz) mp: 84–86° C.

EXAMPLE 7

[$^2$H$_3$, $^{13}$C]Methyl phenyl sulfoxide was prepared as follows. A 30% aqueous solution of hydrogen peroxide (19.53 g; 0.17 moles, 1.2 eq.) was added to a ethanol solution (184 mL) of [$^2$H$_3$, $^{13}$C]methyl phenyl sulfide (18.4 g, 0.14 moles). The reaction was stirred at room temperature for 3 days. After this period the reaction was complete and ethyl acetate (300 mL) was added to the reaction. The reaction was transferred to a separatory funnel and an equal volume of water was added. The organic layer was recovered and the aqueous layer was extracted twice more with ethyl acetate (2×300 mL). The combined organic phases are dried with Na$_2$SO$_4$ then filtered and solvents evaporated. Remaining solvent was removed from the solid under vacuum using a liquid nitrogen cooled trap. [$^2$H$_3$, $^{13}$C]Methyl phenyl sulfoxide (19.45 g; 94%) was obtained as a colorless oil, pure by NMR (>98%), which could be used in subsequent reactions without further purification. $^1$H [CDCl$_3$, 300 MHz] 7.56–7.95 (m, 5H), $^{13}$C [CDCl$_3$, 75 MHz] 43.07 (heptet, J=21 Hz) 123.38, 129.26, 130.94, 145.44.

Although the present invention has been described with reference to specific details, it is not intended that such details should be regarded as limitations upon the scope of the invention, except as and to the extent that they are included in the accompanying claims.

What is claimed is:

1. A labeled compound from the group of [$^2$H$_1$, $^{13}$C], [$^2$H$_2$, $^{13}$C] and [$^2$H$_3$, $^{13}$C]methyl aryl sulfones wherein the $^{13}$C methyl group attached to the sulfur of the sulfone includes exactly one, two or three deuterium atoms and the aryl group is selected from the group consisting of 1-naphthyl, substituted 1-naphthyl, 2-naphthyl, substituted 2-naphthyl, and phenyl groups with the structure:

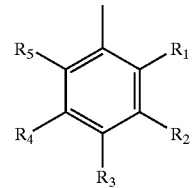

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

2. The compound of claim 1 wherein said aryl is selected from the group consisting of phenyl groups with the structure:

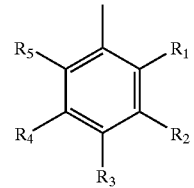

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

3. The compound of claim 1 wherein said aryl is phenyl.

4. The compound of claim 1 wherein said methyl includes exactly one deuterium atom.

5. The compound of claim 1 wherein said methyl includes exactly two deuterium atoms.

6. The compound of claim 1 wherein said methyl includes exactly three deuterium atoms.

7. The compound of claim 3 wherein said methyl includes exactly one deuterium atom.

8. The compound of claim 3 wherein said methyl includes exactly two deuterium atoms.

9. The compound of claim 3 wherein said methyl includes exactly three deuterium atoms.

10. A labeled compound from the group of [$^2$H$_1$, $^{13}$C], [$^2$H$_2$, $^{13}$C] and [$^2$H$_3$, $^{13}$C]methyl aryl sulfoxides wherein the $^{13}$C methyl group attached to the sulfur of the sulfoxide includes exactly one, two or three deuterium atoms and the aryl group is selected from the group consisting of 1-naphthyl, substituted 1-naphthyl, 2-naphthyl, substituted 2-naphthyl, and phenyl groups with the structure:

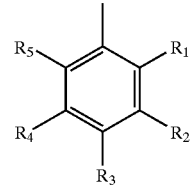

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

11. The compound of claim 10 wherein said aryl is selected from the group consisting of phenyl groups with the structure:

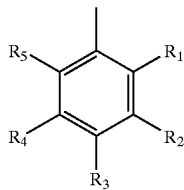

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group.

12. The compound of claim 10 wherein said aryl is phenyl.

13. The compound of claim 10 wherein said methyl includes exactly one deuterium atom.

14. The compound of claim 10 wherein said methyl includes exactly two deuterium atoms.

15. The compound of claim 10 wherein said methyl includes exactly three deuterium atoms.

16. The compound of claim 12 wherein said methyl includes exactly one deuterium atom.

17. The compound of claim 12 wherein said methyl includes exactly two deuterium atoms.

18. The compound of claim 12 wherein said methyl includes exactly three deuterium atoms.

19. A process of preparing a methyl aryl sulfone comprising:

reacting a methyl aryl sulfide sulfoxide with hydrogen peroxide to form a methyl aryl sulfone.

20. The process of claim 19 wherein said methyl includes either a $^{13}C$ atom, or one or more $^2H$ atoms, or both a $^{13}C$ atom and one or more $^2H$ atoms.

21. The process of claim 19 wherein said methyl aryl sulfoxide is selected from the group consisting of [$^2H_1$, $^{13}C$], [$^2H_2$, $^{13}C$] and [$^2H_3$, $^{13}C$]methyl aryl sulfoxides.

22. The process of claim 19 wherein said aryl is selected from the group consisting of 1-naphthyl, substituted 1-naphthyl, 2-naphthyl, substituted 2-naphthyl, and phenyl groups with the structure:

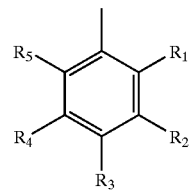

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group.

23. The process of claim 22 wherein said reacting is conducted at room temperature.

* * * * *